(12) United States Patent
Hoying et al.

(10) Patent No.: US 7,648,752 B2
(45) Date of Patent: *Jan. 19, 2010

(54) INVERSE TEXTURED WEB

(75) Inventors: Jody Lynn Hoying, Maineville, OH (US); Luigi Marinelli, Pescara (IT); Nicola D'Alessio, Pescara (IT); Pietro Febo, Pescara (IT)

(73) Assignee: The Procter & Gamble Company, Cincinnati, OH (US)

(*) Notice: Subject to any disclaimer, the term of this patent is extended or adjusted under 35 U.S.C. 154(b) by 30 days.

This patent is subject to a terminal disclaimer.

(21) Appl. No.: 10/737,235

(22) Filed: Dec. 16, 2003

(65) Prior Publication Data

US 2004/0229008 A1   Nov. 18, 2004

Related U.S. Application Data

(63) Continuation-in-part of application No. 10/610,299, filed on Jun. 30, 2003, now abandoned, and a continuation-in-part of application No. 10/435,996, filed on May 12, 2003, now abandoned, each which is a continuation-in-part of application No. 10/324,661, filed on Dec. 20, 2002, now abandoned.

(51) Int. Cl.
*B32B 3/10* (2006.01)
*B32B 3/02* (2006.01)

(52) U.S. Cl. .............. 428/133; 428/92; 428/93; 428/134; 428/136; 428/140; 442/387; 442/389; 442/394

(58) Field of Classification Search .......... 428/85, 428/86, 90, 91, 92, 93; 442/387, 389, 394
See application file for complete search history.

(56) References Cited

U.S. PATENT DOCUMENTS 3,511,740 A    5/1970   Sanders
3,684,284 A *  8/1972   Tranfield ............... 428/91

(Continued)

FOREIGN PATENT DOCUMENTS

DE          43 21 155          1/1995

(Continued)

OTHER PUBLICATIONS

PCT International Search Report dated May 26, 2004.

(Continued)

*Primary Examiner*—Jenna-Leigh Johnson
(74) *Attorney, Agent, or Firm*—Gary J. Foose; Roddy M. Bullock; Angela M. Stone (57) ABSTRACT

A composite web adapted for use as a component in a disposable absorbent article is disclosed. The composite web comprises a first fibrous layer and a second layer, the first and second layers each comprising a body-facing side and a garment-facing side and are disposed in a face to face relationship to form a laminate. The first fibrous layer comprises a fibrous web of randomly oriented fibers with respect to an X-Y plane, and a plurality of discrete regions of fiber reorientation at least on the body-facing side thereof, and a plurality of fibers having portions reoriented in a direction substantially orthogonal to the X-Y plane and extending toward the garment-facing side.

17 Claims, 7 Drawing Sheets

U.S. PATENT DOCUMENTS

| | | | |
|---|---|---|---|
| 3,695,270 | A | 10/1972 | Dostal |
| 4,042,453 | A | 8/1977 | Conway |
| 4,379,799 | A | 4/1983 | Holmes |
| 4,465,726 | A | 8/1984 | Holmes |
| 4,596,567 | A | 6/1986 | Iskra |
| 5,062,418 | A | 11/1991 | Dyer |
| 5,180,620 | A * | 1/1993 | Mende ................ 428/138 |
| 5,382,245 | A | 1/1995 | Thompson |
| 5,508,080 | A * | 4/1996 | Sorimachi et al. ........ 428/86 |
| 5,518,801 | A | 5/1996 | Chappell |
| 5,554,145 | A | 9/1996 | Roe |
| 5,628,097 | A | 5/1997 | Benson |
| 5,650,214 | A | 7/1997 | Anderson et al. |
| 5,658,639 | A | 8/1997 | Curro |
| 5,700,255 | A | 12/1997 | Curro et al. |
| 5,730,738 | A | 3/1998 | McFall et al. |
| 5,792,404 | A | 8/1998 | Cree et al. |
| 5,876,391 | A | 3/1999 | Roe et al. |
| 5,916,661 | A | 6/1999 | Benson |
| 5,932,316 | A | 8/1999 | Cree et al. |
| 5,968,029 | A | 10/1999 | Chappell |
| 5,993,432 | A | 11/1999 | Lodge |
| 6,025,535 | A | 2/2000 | Octavio et al. |
| 6,048,600 | A * | 4/2000 | Hansson ................ 428/136 |
| 6,103,376 | A | 8/2000 | Phillips et al. |
| 6,120,718 | A * | 9/2000 | Kotek et al. ............ 264/209.1 |
| 6,458,447 | B1 | 10/2002 | Cabell |
| 6,733,610 | B2 | 5/2004 | Mizutani et al. |
| 2002/0082574 | A1 | 6/2002 | Nakashita |
| 2004/0022993 | A1* | 2/2004 | Wildeman ............... 428/92 |
| 2004/0157036 | A1* | 8/2004 | Provost et al. ........... 428/85 |

FOREIGN PATENT DOCUMENTS

| | | |
|---|---|---|
| FR | 2 713 083 A1 | 6/1995 |
| FR | 2713083 A1 | 6/1995 |
| WO | WO 01/45616 A1 | 6/2001 |
| WO | WO 01/76523 A2 | 10/2001 |
| WO | WO 02/076723 A1 | 10/2002 |
| WO | WO 02/100632 A1 | 12/2002 |

OTHER PUBLICATIONS

Office Action for U.S. Appl. No. 12/370,850, dated Jul. 8, 2009; P&G Case 9683MC; Turner et al.; filing date Feb. 13, 2009.
Office Action for U.S. Appl. No. 11/158,165, dated May 16, 2008; P&G Case 9683M; Turner et al.; filing date Jun. 21, 2005.
Office Action for U.S. Appl. No. 11/158,165, dated Dec. 7, 2007; P&G Case 9683M; Turner et al.; filing date Jun. 21, 2005.
Office Action for U.S. Appl. No. 11/158,165, dated Jul. 3, 2007; P&G Case 9683M; Turner et al; filing date Jun. 21, 2005.
Office Action for U.S. Appl. No. 11/157,770, dated Apr. 28, 2009; P&G Case 9682M; Hammons et al.; filing date Jun. 21, 2005.
Office Action for U.S. Appl. No. 11/157,770, dated Jun. 2, 2008; P&G Case 9682M; Hammons et al.; filed Jun. 21, 2005.
Office Action for U.S. Appl. No. 11/157,770, dated Oct. 1, 2007; P&G Case 9682M; Hammons et al.; filing date Jun. 21, 2005.
Office Action for U.S. Appl. No. 11/156,020, dated Jul. 8, 2009; P&G Case 9681M; Curro et al.; filing Jun. 17, 2005.
Office Action for U.S. Appl. No. 11/156,020, dated Dec. 24, 2008; P&G Case 9681M; Curro et al.; filing date Jun. 17, 2005.
Office Action for U.S. Appl. No. 11/156,020, dated Jul. 10, 2008; P&G Case 9681M; Curro et al.; filing date Jun. 17, 2005.
Office Action for U.S. Appl. No. 11/156,020, dated Nov. 27, 2007; P&G Case 9681M; Curro et al.; filing date Jun. 17, 2005.
Office Action for U.S. Appl. No. 11/156,020, dated Jun. 20, 2007; P&G Case 9681M; Curro et al.; filing date Jun. 17, 2005.
Office Action for U.S. Appl. No. 11/156,020, dated Jan. 2, 2007; P&G Case 9681M; Curro et al.; filing date Jun. 17, 2005.
Examiner's Answer for U.S. Appl. No. 11/155,805, dated Aug. 6, 2009; P&G Case 9680M; Curro et al.; filing date Jun. 17, 2005.
Office Action for U.S. Appl. No. 11/155,805, dated Oct. 30, 2008; P&G Case 9680M; Curro et al.; filing date Jun. 17, 2005.
Office Action for U.S. Appl. No. 11/155,805, dated May 16, 2008; P&G Case 9680M; Curro et al.; filing date Jun. 17, 2005.
Office Action for U.S. Appl. No. 11/155,805, dated Nov. 27, 2007; P&G Case 9680M; Curro et al., filing date Jun. 17, 2005.
Office Action for U.S. Appl. No. 11/155,805, dated Jun. 19, 2007; P&G Case 9680M; Curro et al.; filing date Jun. 17, 2005.
Office Action for U.S. Appl. No. 11/650,821, dated Mar. 16, 2009; P&G Case 9455C; Hoying et al.; filing date Jan. 8, 2007.
Office Action for U.S. Appl. No. 11/650,821, dated Oct. 8, 2008; P&G Case 9455C; Hoying et al.; filing date Jan. 8, 2007.
Office Action for U.S. Appl. No. 11/650,821, dated Apr. 23, 2008; P&G Case 9455C; Hoying et al.; filing date Jan. 8, 2007.
Office Action for U.S. Appl. No. 11/650,821, dated Oct. 16, 2007; P&G Case 9455C; Hoying et al.; filing date Jan. 8, 2007.
Notice of Allowance for U.S. Appl. No. 10/737,307, dated Sep. 28, 2006; P&G Case 9455; Hoying et al.; filing date Dec. 16, 2003.
Office Action for U.S. Appl. No. 10/737,307, dated May 31, 2006; P&G Case 9455; Hoying et al.; filing date Dec. 16, 2003.
Office Action for U.S. Appl. No. 10/737,307, dated Oct. 7, 2005; P&G Case 9455; Hoying et al.; filing date Dec. 16, 2003.
Notice of Allowance for U.S. Appl. No. 10/980,219, dated May 23, 2007; P&G Case 9313RR; Broering et al.; filing date Nov. 3, 2004.
Office Action for U.S. Appl. No. 10/980,219, dated Mar. 5, 2007; P&G Case 9313RR; Broering et al.; filing date Nov. 3, 2004.
Office Action for U.S. Appl. No. 10/980,219, dated Sep. 11, 2006; P&G Case 9313RR; Broering et al.; filing date Nov. 3, 2004.
Notice of Allowance for U.S. Appl. No. 10/737,430 dated Mar. 18, 2008; P&G Case 9313R; Curro et al.; filing date Dec. 16, 2003.
Notice of Allowance for U.S. Appl. No. 10/737,430, dated Oct. 29, 2007; P&G Case 9313R; Curro et al.; filing date Dec. 16, 2003.
Office Action for U.S. Appl. No. 10/737,430 dated Jul. 16, 2007; P&G Case 9313R; Curro et al.; filing date Dec. 16, 2003.
Office Action for U.S. Appl. No. 10/737,430, dated Jan. 25, 2007; P&G Case 9313R; Curro et al.; filing date Dec. 16, 2003.
Office Action for U.S. Appl. No. 10/737,430, dated Aug. 8, 2006; P&G Case 9313R; Curro et al.; filing date Dec. 16, 2003.
Office Action for U.S. Appl. No. 10/737,430, dated Feb. 3, 2006; P&G Case 9313R; Curro et al.; filing date Dec. 16, 2003.
Office Action for U.S. Appl. No. 10/737,430, dated Aug. 24, 2005; P&G Case 9313R; Curro et al.; filing date Dec. 16, 2003.
Office Action for U.S. Appl. No. 12/021,369, dated Jun. 25, 2009; P&G Case 9313RC; Curro et al.; filing dated Jan. 29, 2008.
Office Action for U.S. Appl. No. 10/737,306, dated Jun. 12, 2008; P&G Case 9134R2; Gray et al.; filing date Mar. 28, 2003.
Notice of Allowance for U.S. Appl. No. 10/737,306, dated Nov. 29, 2007; P&G Case 9134R2; Gray et al.; filing date Mar. 28, 2003.
Office Action for U.S. Appl. No. 10/737,306, dated Jul. 16, 2007; P&G Case 9134R2; Gray et al.; filing date Mar. 28, 2003.
Office Action for U.S. Appl. No. 10/737,306, dated Jan. 27, 2007; P&G Case 9134R2; Gray et al.; filing date Mar. 28, 2003.
Office Action for Appl. No. 10/737,306, dated Aug. 9, 2006; P&G Case 9134R2; Gray et al.; filing date Mar. 28, 2003.
Office Action for U.S. Appl. No. 10/737,306, dated Aug. 24, 2005; P&G Case 9134R2; Gray et al.; filing date Mar. 28, 2003.
Office Action for U.S. Appl. No. 10/737,306, dated Feb. 3, 2006; P&G Case 9134R2; Gray et al.; filing date Mar. 28, 2003.
Office Action for U.S. Appl. No. 11/129,877, dated Mar. 30, 2007; P&G Case 9684M; Cabell; filing date May 16, 2005.
Office Action for U.S. Appl. No. 11/129,877, dated Oct. 2, 2007; P&G Case 9684M; Cabell; filing date May 16, 2005.
Office Action for U.S. Appl. No. 11/129,877, dated Jan. 23, 2008; P&G Case 9684M; Cabell; filing date May 16, 2005.
Office Action for U.S. Appl. No. 11/129,877, dated Jun. 12, 2008; P&G Case 9684M; Cabell; filing date May 16, 2005.

* cited by examiner

Fig. 12

INVERSE TEXTURED WEB

CROSS-REFERENCE TO RELATED APPLICATION

This application is a continuation-in-part of U.S. application Ser. No. 10/610,299, filed Jun. 30, 2003, now abandoned, and a continuation-in-part of U.S. application Ser. No. 10/435,996, filed May 12, 2003, now abandoned, both of which are a continuation-in-part of prior U.S. application Ser. No. 10/324,661, filed Dec. 20, 2002, now abandoned,

FIELD OF INVENTION

This invention relates to webs such as films and fibrous woven and nonwoven webs. In particular, this invention relates to laminates of such webs treated by mechanical formation to have improved fluid handling properties for use in disposable absorbent articles.

BACKGROUND OF THE INVENTION

Disposable absorbent articles such as disposable diapers, incontinence products, catamenial products and the like are widely used, and much effort has been made to improve the effectiveness and functionality of these articles. In general such articles have a fluid permeable body-facing layer, often referred to as a topsheet, a fluid impermeable garment-facing layer, often referred to as a backsheet, and a fluid storage member, often referred to as an absorbent core, sandwiched between the topsheet and the backsheet. Other components, such as acquisition layers, secondary topsheets, and adhesive fasteners are also well known in the art.

It is known to make laminates of web materials to combine the fluid handling properties of each into an improved fluid handling composite material. For example, it is known to combine into a laminate two nonwoven materials by needlepunching to produce integrally-bonded and entangled nonwoven webs. This process is often simply referred to as "needling." U.S. Pat. No. 5,080,951 granted Jan. 14, 1992 to Guthrie, for example, discloses a nonwoven web composed of multiple layers bonded by a needling process that causes some fibers to extend through the entire thickness of the fabric and beyond the surface, thereby leaving short segments of filaments protruding from the exterior surface of the web. Frequently hydroentangling is used to accomplish a similar entangling of two fibrous nonwoven webs. Needling, like fluid entangling, is a relatively slow and therefore expensive process for manufacture of nonwoven webs, particularly for webs intended for disposable article use.

Needling, hydroentangling can be used to provide for texture to an otherwise flat web such as nonwovens. Additionally, other techniques such as passing a web through the nip of counter-rotating patterned rolls can be used to impart texture to a film or nonwoven web. Such texture is generally beneficial as the body-contacting portion of an article such as a garment or a disposable absorbent article. For example, commonly-assigned U.S. Ser. No. 10/720,557 filed Sep. 24, 2003 in the name of Hammons et al. which claims priority to U.S. Provisional Application No. 60/434,792 filed Dec. 18, 2002 in the name of Hammons, et al., discloses textured body-facing layers for sanitary napkins that improve fluid acquisition and result in the wearer having a clean body. In Hammons et al. the texture includes raised portions that contact the skin of the wearer to act as wipers to acquire fluid from the body.

There remains, however, a need for components of disposable absorbent articles having improved fluid handling properties.

Additionally, there is a need for a method of relatively inexpensively making components of disposable absorbent articles having improved fluid handling properties.

SUMMARY OF THE INVENTION

A composite web adapted for use as a component in a disposable absorbent article is disclosed. The composite web comprises a first fibrous layer and a second layer, the first and second layers each comprising a body-facing side and a garment-facing side and are disposed in a face to face relationship to form a laminate. The first fibrous layer comprises a fibrous web of randomly oriented fibers with respect to an X-Y plane, and a plurality of discrete regions of fiber reorientation at least on the body-facing side thereof, and a plurality of fibers having portions reoriented in a direction substantially orthogonal to the X-Y plane and extending toward the garment-facing side.

DETAILED DESCRIPTION OF THE INVENTION

Figure 1:
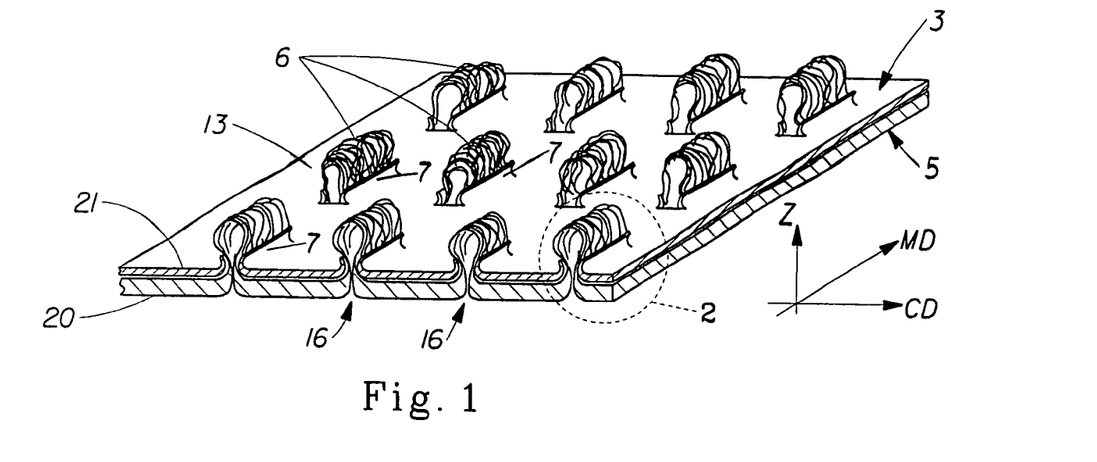
FIG. 1 is a perspective view of a web suitable for use in an article of the present invention.

FIG. 1 shows a laminate web 1 suitable for use in an article of the present invention, hereinafter referred to simply as web 1. Web 1 comprises at least two layers. The layers are referred to herein as generally planar, two-dimensional precursor webs, such as first precursor web 20 and second precursor web 21. Either precursor web can be a film, a nonwoven, or a woven web. Precursor webs 20 and 21 (and any additional webs) can be joined by adhesive, thermal bonding, ultrasonic bonding and the like, but are preferably joined without the use of adhesive or other forms of bonding. As disclosed below, the constituent precursor webs of web 1 can be joined by interlocking mechanical engagement resulting from the formation of tufts 6.

Web 1 has a first side 3 and a second side 5, the term "sides" being used in the common usage of generally planar two-dimensional webs, such as paper and films that have two sides when in a generally flat condition. In use first side 3 is a garment-facing side and second side 5 is a body-facing side. Each precursor web 20 and 21 has a first surface 12 and 13, respectively, and a second surface 14 and 15, respectively (shown in FIG. 3). Web 1 has a machine direction (MD) and a cross machine direction (CD) as is commonly known in the art of web manufacture. Although the present invention can be practiced with polymer films and woven webs, in a preferred embodiment first precursor web 20 is a nonwoven web comprised of substantially randomly oriented fibers. By "substantially randomly oriented" is meant that, due to processing conditions of the precursor web, there may be a higher amount of fibers oriented in the MD than the CD, or vice-versa. For example, in spunbonding and meltblowing processes continuous strands of fibers are deposited on a support moving in the MD. Despite attempts to make the orientation of the fibers of the spunbond or meltblown nonwoven web truly "random," usually a slightly higher percentage of fibers are oriented in the MD as opposed to the CD. In a preferred embodiment, second precursor web 21 is a nonwoven web similar to the first precursor web 20, or a polymer film, such as a polyethylene film.

Figure 3:
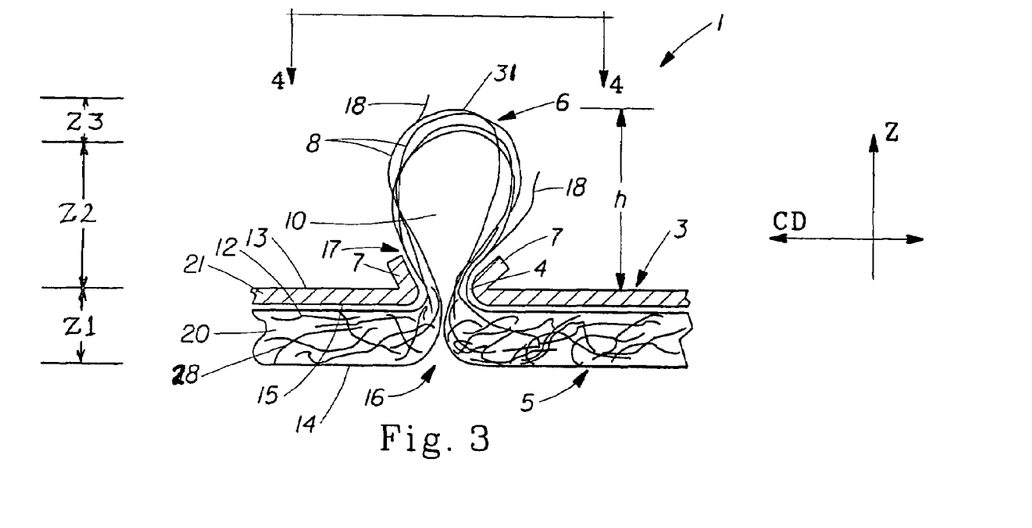
FIG. 3 is a cross-sectional view of section 3-3 of FIG. 2.

In one embodiment, first side 3 of web 1 is defined by exposed portions of the first surface 13 of second precursor web 21 and at least one, but preferably a plurality of, discrete tufts 6 which are integral extensions of the fibers of a nonwoven first precursor web 20. Each tuft 6 can comprise a plurality of looped, aligned fibers 8 extending through second precursor web 21 and outwardly from the first surface 13 thereof. In another embodiment each tuft 6 can comprise a plurality of non-looped fibers 18 (as shown in FIG. 3) that extend outwardly from the first surface 13. In another embodiment, each tuft 6 can comprise a plurality of fibers which are integral extensions of the fibers of both a nonwoven first precursor web 20 and a nonwoven second precursor web 21. Since first side 3 is the garment-facing side of a component of a disposable absorbent article, the first side is internal to the article and is referred to herein as "inverse texture." That is, the texture provided by the tufts 6 is internal to the article In another embodiment, second precursor web 21 has sufficient caliper (i.e., thickness) such that tufts 6 don't actually push through second precursor web 21 but simply push into second precursor web 21 such that no tufts are visible from the outside of web 1. Again, therefore, the tufts 6 are internal to the web 1 and referred to herein as "inverse texture."

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, air laying processes, meltblowing processes, spunbonding processes, spunlacing processes, hydroentangling, and bonded carded web processes, including carded thermal bonding. The basis weight of nonwoven fabrics is usually expressed in grams per square meter (gsm). The basis weight of the laminate web is the combined basis weight of the constituent layers and any other added components. Fiber diameters are usually expressed in microns; fiber size can also be expressed in denier, which is a unit of weight per length of fiber. The basis weight of laminate webs suitable for use in an article of the present invention can range from 10 gsm to 100 gsm, depending on the ultimate use of the web 1.

The constituent fibers of nonwoven precursor webs 20 and/or 21 can be polymer fibers as known in the art. The fibers can be monocomponent, bicomponent, and/or biconstituent, non-round (e.g., capillary channel fibers), and can have major cross-sectional dimensions (e.g., diameter for round fibers) ranging from 0.1-500 microns. The constituent fibers of the nonwoven precursor webs may also be a mixture of different fiber types, differing in such features as chemistry (e.g. PE and PP), components (mono- and bi-), shape (i.e. capillary channel and round) and the like. The constituent fibers can range from about 0.1 denier to about 100 denier.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky, to form a web of randomly dispersed meltblown fibers. Meltblown fibers are microfibers which may be continuous or discontinuous and are generally smaller than 10 microns in average diameter.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multi-constituent fibers.

As used herein, the term "non-round fibers" describes fibers having a non-round cross-section, and include "shaped fibers" and "capillary channel fibers" as are known in the art. Such fibers can be solid or hollow, and they can be tri-lobal, delta-shaped, and are preferably fibers having capillary channels on their outer surfaces. The capillary channels can be of various cross-sectional shapes such as "U-shaped", "H-shaped", "C-shaped" and "V-shaped". One preferred capillary channel fiber is T-401, designated as 4DG fiber available from Fiber Innovation Technologies, Johnson City, Tenn. T-401 fiber is a polyethylene terephthalate (PET).

As used herein, the term "integral" as in "integral extension" when used of the tufts 6 refers to fibers of the tufts 6 having originated from the fibers of the precursor webs 20 and/or 21. Therefore, the looped fibers 8 and non-looped fibers 18 of tufts 6, can be plastically deformed and extended fibers of the first precursor web 20, and are, therefore, integral with first precursor web 20. Similarly, for embodiments wherein second precursor web 21 is a nonwoven comprising similarly extensible fibers, the fibers of second precursor web 21 can contribute to tufts 6. As used herein, "integral" is to be distinguished from fibers introduced to or added to a separate precursor web for the purpose of making tufts, as is commonly done in conventional carpet making, for example.

First precursor web 20 can be a fibrous woven or nonwoven web comprising fibers having sufficient elongation properties to have portions formed into tufts 6. As described more fully below, tufts are formed by urging fibers out-of-plane in the Z-direction at discrete, localized, portions of first precursor web 20. The urging out-of-plane can be due to fiber displacement, i.e., the fiber is able to move relative to other fibers and be "pushed," so to speak, out-of-plane. More often, however, for most nonwoven first precursor webs 20, the urging out-of-plane is due to the fibers of tufts 6 having been at least partially plastically stretched and permanently deformed to form tufts 6. Therefore, in one embodiment, depending on the desired height of tufts 6, the constituent fibers of a nonwoven first precursor webs 20 can exhibit an elongation to break of at least about 5%, more preferably at least about 10%, more preferably at least about 25%, more preferably at least about 50%, and more preferably at least about 100%. Elongation to break can be determined by simple tensile testing, such as by use of Instron tensile testing equipment, and can generally be found on material data sheets from suppliers of such fibers or webs.

It can be appreciated that a suitable nonwoven first precursor web 20 should comprise fibers capable of experiencing sufficient plastic deformation and tensile elongation, or are capable of sufficient fiber mobility, such that looped fibers 8 are formed. However, it is recognized that a certain percentage of fibers urged out of the plane of the first surface 12 of first precursor web 20 will not form a loop, but instead will break and form loose ends. Such fibers are referred to herein as "loose" fibers or "loose fiber ends" 18 as shown in FIG. 3. Loose fiber ends 18 are not necessarily undesirable for the present invention, and in some embodiments, most or-all of the fibers of tufts 6 can be loose fiber ends 18. Loose fiber ends 18 can also be the result of forming tufts 6 from nonwoven webs consisting of, or containing, cut staple fibers. In such a case, some number of the staple fiber ends may protrude into the tuft 6, depending upon such things as the number of staple fibers in the web, the staple fiber cut length, and the height of the tufts.

First precursor web 20 can be a fibrous woven or nonwoven web comprising elastic or elastomeric fibers. Elastic or elastomeric fibers can be stretched at least about 50% and return to within 10% of their original dimension. Tufts 6 can be formed from elastic fibers if the fibers are simply displaced due to the mobility of the fiber within the nonwoven, or if the fibers are stretched beyond their elastic limit and are plastically deformed.

For use as a topsheet in the present invention, first precursor web 20 can be relatively hydrophobic compared to second precursor web 21. Therefore, fluid to be absorbed through the topsheet can collect in the void volume of each tuft and transported into a relatively more hydrophilic second precursor web 21 to underlying components of an article of the present invention. While actual measures of hydrophilicity or hydrophobicity are not considered to be critical (only relative hydrophilicity/hydrophobicity between the first precursor web 20 and the second precursor web 21), in general, first precursor web 20 can be considered hydrophobic if it exhibits a contact angle with water greater than about 70 degrees. If second precursor web is not naturally hydrophilic (i.e., the polymer properties are not hydrophilic), it can be rendered hydrophilic by methods known in the art, for example, by application of a surfactant to the fibers and/or the web.

For use as a topsheet in an absorbent article, second precursor web 21 can be virtually any web material, the only preference being that it be more hydrophilic relative to first precursor web 20, and that it have sufficient integrity to be formed into a laminate by the process described below. In one embodiment, second precursor web can be a film or a nonwoven web having sufficiently less elongation properties relative to first precursor web 20, such that upon experiencing the strain of fibers from first precursor web 20 being urged out-of-plane in the direction of second precursor web 21, second precursor web 21 will rupture, e.g., by tearing due to extensional failure, such that portions of first precursor web 20 can extend through, (i.e., "punch through" so to speak), second precursor web 21 to form tufts 6 on first side 3 of web 1, as shown in FIG. 1. In one embodiment second precursor web 21 can be a polymer film. In one embodiment second precursor web can be an apertured polymer film. In one embodiment second precursor web 21 can be a nonwoven web.

Figure 2:
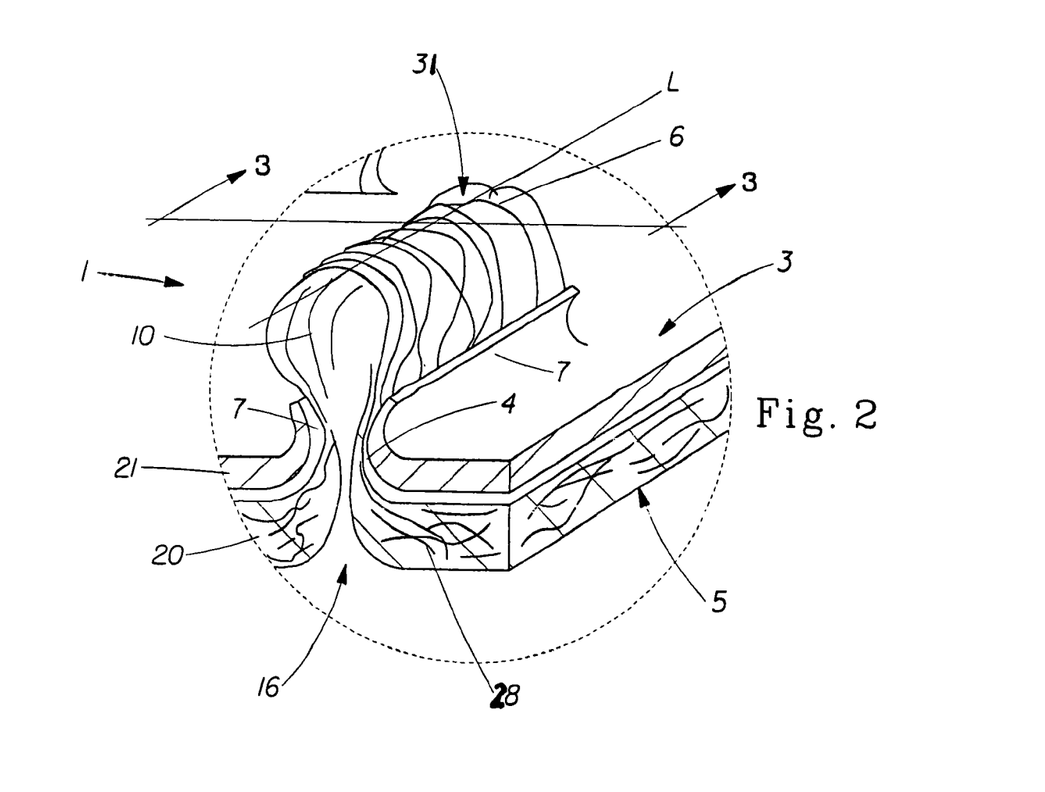
FIG. 2 is an enlarged view of a portion of the web shown in FIG. 1.

A representative tuft 6 for the embodiment of web 1 shown in FIG. 1 is shown in a further enlarged view in FIG. 2. The embodiment shown in FIG. 2 is one in which the tuft is not internally buried in second precursor web 21 but extends through second precursor web 21. As shown, tuft 6 comprises a plurality of looped fibers 8 that are substantially aligned such that tuft 6 has a distinct linear orientation and a longitudinal axis L. Tuft 6 also has a transverse axis T generally orthogonal to longitudinal axis L in the MD-CD plane. In the embodiment shown in FIGS. 1 and 2, longitudinal axis L is parallel to the MD. In one embodiment, all the spaced apart tufts 6 have generally parallel longitudinal axes L. The number of tufts 6 per unit area of web 1, i.e., the area density of tuft 6, can be varied from 1 tuft per unit area, e.g., square centimeter to as high as 100 tufts per square centimeter. There can be at least 10, or at least 20 tufts 6 per square centimeter, depending on the end use. In general, the area density need not be uniform across the entire area of web 1, but tufts 6 can be only in certain regions of web 1, such as in regions having predetermined shapes, such as lines, stripes, bands, circles, and the like.

As can be appreciated by the description herein, in many embodiments of web 1 openings 4 will have a distinct linear orientation and a longitudinal axis, which is oriented parallel to the longitudinal axis L of its corresponding tuft 6. Likewise, openings 4 will also have a transverse axis generally orthogonal to longitudinal axis in the MD-CD plane. As can also be appreciated, in embodiments where the caliper of second precursor web 21 is greater than the height h of tuft 6, opening 4 will only be on second surface 15 of second precursor web 21, and not extend all the way through second precursor web 21. In one embodiment, tufts 6 can make bulges on first surface 14 of second precursor web 21.

As shown in FIGS. 1-4, tufts 6 can extend through openings 4 in second precursor web 21. Openings 4 can be formed by locally rupturing second precursor web 21 by the process described in detail below, or by urging fibers of second precursor web 21 out of plane in like manner as fibers 8. Rupture may involve a simple splitting open of second precursor web 21, such that opening 4 remains a simple two-dimensional aperture. However, for some materials, such as polymer films, portions of second precursor web 21 can be deflected or urged out-of-plane (i.e., the plane of second precursor web 21) to form flap-like structures, referred to herein as flap, or flaps, 7. The form and structure of flaps 7 is highly dependent upon the material properties of second precursor web 21. Flaps 7 can have the general structure of one or more flaps, as shown in FIGS. 1 and 2. In other embodiments, flap 7 can have a more volcano-like structure, as if the tuft 6 is erupting from the flap 7.

Tufts 6 can be, in a sense, "punched through" at least a portion of second precursor web 21 and can be "locked" in place by frictional engagement with openings 4. In some embodiments, for example, the lateral width of opening 4 (i.e., the dimension measured parallel to its transverse axis) can be less than the maximum width of the tooth that formed the opening (per the process described below). This indicates a certain amount of recovery at the opening that tends to constrain tuft 6 from pulling back out through opening 4. The frictional engagement of the tufts and openings provides for a laminate web structure having permanent tufting on one side that can be formed without adhesives or thermal bonding.

Tufts 6 can be spaced sufficiently closely so as to effectively cover first side 3 of web 1. In such an embodiment, both sides of web 1 appear to comprise nonwoven fibers integral with first precursor web 20, with a difference between the two sides 3 and 5 being a difference in surface texture. Therefore, in one embodiment, a topsheet of the present invention can be described as a laminate material of two or more precursor webs, wherein both sides of the laminate web are substantially covered by fibers from only one of the precursor webs. Specifically, a topsheet of the present invention can be described as comprising a first relatively hydrophobic component (i.e., second precursor web 21) and a second relatively hydrophilic component (i.e., first precursor web 20) wherein the relatively hydrophilic component extends through the relatively hydrophobic component from a body facing side to a garment facing side and is therefore disposed on both sides (i.e., sides 3 and 5) of the topsheet.

As shown in FIGS. 1-4, one characteristic of tufts 6 can be the predominant directional alignment of the fibers 8 or 18. For example, looped, aligned fibers 8 can be described as having a significant or major vector component parallel to the Z-CD plane and the looped fibers 8 have a substantially uniform alignment with respect to transverse axis T when viewed in plan view, such as in FIG. 4. By "looped" fibers 8 is meant fibers 8 that are integral with and begin and end in first precursor web 20 and/or second precursor web 21 but extend outwardly in the Z-direction from first side 3 of web 1. By "aligned" with respect to looped fibers 8 of tufts 6 is meant that looped fibers 8 are all generally oriented such that, if viewed in plan view as in FIG. 4, each of the looped fibers 8 has a significant vector component parallel to the transverse axis T, and preferably a major vector component parallel to the transverse axis T. Although only fibers from first precursor web 20 are shown in FIGS. 1-4, it is to be understood that this is because in these FIGS. a film/nonwoven web 1 is depicted, in which the elongation properties of the web result in tensile failure to form opening 4 through which fibers 8 and/or 18 can protrude. It is understood that if a nonwoven/nonwoven web 1 were depicted, fibers from each of precursor webs 20 and 21 could form tufts 6, and, in such a structure, the tufts 6 could exhibit a substantially layered structure, the fibers of first precursor web 20 being generally internally-disposed in tufts 6.

In contrast, non-looped fibers 18 are integral with, but only begin in first or second precursor webs 20 and/or 21 and have a free end extending outwardly in the Z-direction from first side 3 of web 1. Loose fibers 18 can also have a generally uniform alignment described as having a significant or major vector component parallel to the Z-CD plane.

Figure 4:
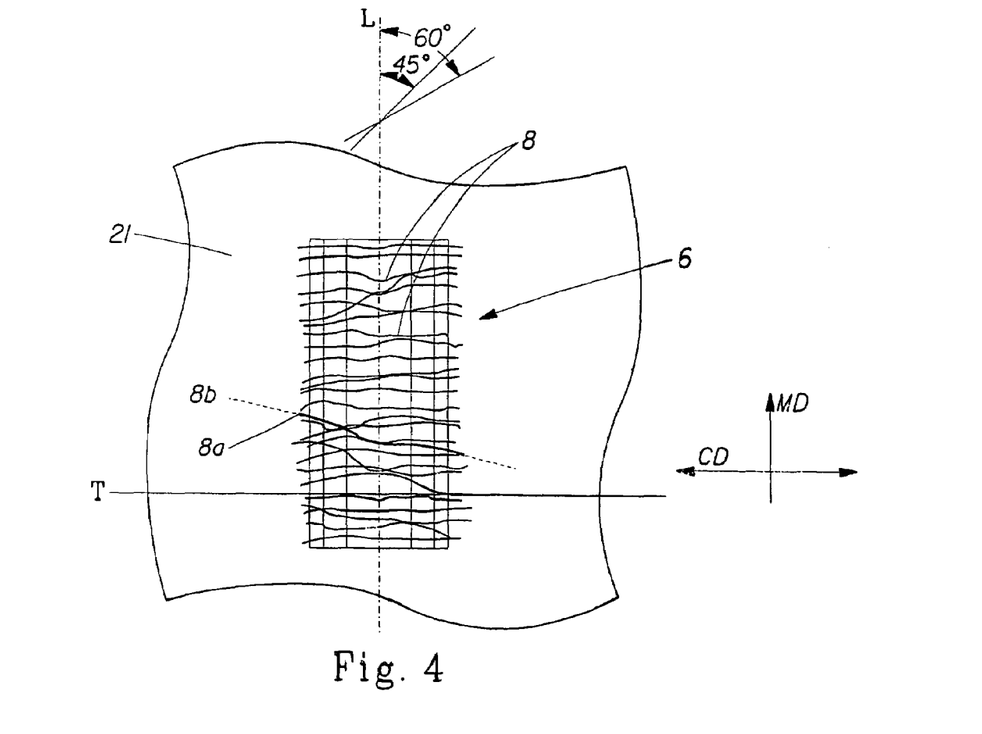
FIG. 4 is a plan view of a portion of the web as indicated by 4-4 in FIG. 3.

For both looped fibers 8 and loose fibers 18, the alignment is a characteristic of tufts 6 prior to any post-manufacture deformation due to winding onto a roll, or compression in use in an article of manufacture. As used herein, a looped fiber 8 oriented at an angle of greater than 45 degrees from the longitudinal axis L when viewed in plan view, as in FIG. 4, has a significant vector component parallel to the transverse axis T. As used herein, a looped fiber 8 oriented at an angle of greater than 60 degrees from longitudinal axis L when viewed in plan view, as in FIG. 4, has a major vector component parallel to the transverse axis T. In a preferred embodiment, at least 50%, more preferably at least 70%, and more preferably at least 90% of fibers 8 of tuft 6 have a significant, and more preferably, a major vector component parallel to transverse axis T. Fiber orientation can be determined by use of magnifying means if necessary, such as a microscope fitted with a suitable measurement scale. In general, for a non-linear segment of fiber viewed in plan view, a straight-line approximation for both longitudinal axis L and the looped fibers 8 can be used for determining the angle of looped fibers 8 from longitudinal axis L. For example, as shown in FIG. 4, one fiber 8a is shown emphasized by a heavy line, and it's linear approximation 8b is shown as a dashed line. This fiber makes an angle of approximately 80 degrees with the longitudinal axis (measured counterclockwise from L).

The orientation of looped fibers 8 in the tufts 6 is to be contrasted with the fiber composition and orientation for first or second precursor webs 20 and 21 (if a nonwoven web is used for second precursor web 21), which, for nonwoven webs is best described as having a substantially randomly-oriented fiber alignment. In a woven web embodiment, the orientation of the looped fibers 8 in tufts 6 could be the same as described above, but the fibers of woven precursor webs would have the orientation associated with the particular weaving process used to make the web, e.g., a square weave pattern.

In the embodiment shown in FIG. 1 the longitudinal axes L of tufts 6 are generally aligned in the MD. Tufts 6 and, therefore, longitudinal axes L, can, in principle, be aligned in any orientation with respect to the MD or CD. Therefore, in general, it can be said that for each tuft 6, the looped aligned fibers 8 are aligned generally orthogonal to the longitudinal axis L such that they have a significant vector component parallel to transverse axis T, and more preferably a major vector component parallel to transverse axis T.

In some embodiments, due to the preferred method of forming tufts 6, as described below, another characteristic of tufts 6 comprising predominantly looped, aligned fibers 8, can be their generally open structure characterized by open void area 10 defined interiorly of tufts 6. By "void area" is not meant an area completely free of any fibers; the term is meant as a general description of the general appearance of tufts 6. Therefore, it may be that in some tufts 6 a loose fiber 18 or a plurality of loose fibers 18 may be present in the void area 10. By "open" void area is meant that the two longitudinal ends of tuft 6 are generally open and free of fibers, such that tuft 6 can form something like a "tunnel" structure in an uncompressed state, as shown in FIG. 3.

One way of describing the structure of web 1 is with respect to the three-dimensional fiber orientation in the Z-direction, as shown in FIG. 3, for example. As shown in FIG. 3, at least three "zones" can be identified, with each zone being identified with a portion of web 1 in the Z-direction. A lowermost portion of web 1 designated as zone 1, Z1, extend generally from lower surface 14 of first precursor web 1 to the upper surface 13 of second precursor web 21 and comprises substantially non-reoriented fibers of the first and second precursor webs. The fibers of Z1 are substantially horizontally-oriented with respect to the CD-MD plane with very little Z-directionality. Zone 2, Z2, extends generally from the first surface 13 of second precursor web 21 to the interior limit of void area 10 and comprises substantially reoriented fibers that are substantially vertically-oriented with respect to the CD-MD plane, that is, fibers in zone Z2 are oriented predominantly in the Z direction and have very little CD or MD directionality. In Zone 3, Z3, which comprises the fibers of distal portion 31 of tuft 6, fibers are again oriented generally horizontally with respect to the CD-MD plane. Therefore, in one embodiment, web 1 can be described structurally as a nonwoven web, which in a generally flat condition defining a plane of the web, the web comprising tufted regions, the tufted regions having three zones, each zone characterized by the zone fiber orientation, wherein the first and third zones comprise fibers having a first orientation substantially parallel to the plane of the web, and a second zone intermediate to and joining the first and third zones, the second zone comprising fibers having second orientation, the second orientation being substantially orthogonal to the first plane of the web, that is, having substantially no portions oriented substantially parallel to the first plane of the web.

In one preferred embodiment of web 1 for use as a topsheet on a disposable article, both precursor webs 20 and 21 are nonwoven webs, with second precursor web 21 being relatively hydrophobic with respect to first precursor web 20 (and, preferably, the skin or hair of the wearer), and both contribute fibers to tufts 6 in a relatively layered manner. In such a topsheet, as described more fully below with respect to FIG. 10, a large portion, if not all, of the fibers in closest proximity to the skin of the wearer can be relatively hydrophilic to wick fluid away from the body and through relatively hydrophobic second precursor web 21 that then can help prevent rewet to the skin.

As a consequence of a preferred method of making web 1, the second side 5 of web 1 exhibits discontinuities 16 characterized by a generally linear indentation defined by formerly random fibers of the second surface 14 of first precursor web 20 having been urged directionally (i.e., in the "Z-direction" generally orthogonal to the MD-CD plane as shown in FIGS. 1 and 3) into tufts 6 by the teeth of the forming structure, described in detail below. The abrupt change of orientation exhibited by the previously randomly-oriented fibers of first precursor web 20 defines the discontinuity 16, which exhibits a linearity such that it can be described as having a longitudinal axis generally parallel to longitudinal axis L of the tuft 6. Due to the nature of many nonwoven webs useful as first precursor webs 20, discontinuity 16 may not be as distinctly noticeable as tufts 6. For this reason, the discontinuities 16 on the second side 5 of web 1 can go unnoticed and may be generally undetected unless web 1 is closely inspected. As such, the second side 5 of web 1 can have the look and feel of an un-tufted first precursor web 20. Thus in some embodiments, web 1 can have the textured look and feel of terry cloth on first side 3, and a relatively smooth, soft look and feel on second side 5, both sides being comprised of fibers from the same nonwoven web, i.e., the first precursor web 20. In other embodiments, discontinuities 16 can appear as apertures, and may be apertures through web 1 via the ends of the tunnel-like tufts 6.

From the description of web 1 comprising at least a nonwoven first precursor web 20, it can be seen that the fibers 8 or 18 of tuft 6 can originate and extend from either the first surface 12 or the second surface 14 of first precursor web 20. Of course the fibers 8 or 18 of tuft 6 can also extend from the interior 28 of first precursor web 20. The fibers 8 or 18 of tufts 6 extend due to having been urged out of the generally two-dimensional plane of first precursor web 20 (i.e., urged in the "Z-direction" as shown in FIG. 3). In general, the fibers 8 or 18 of the tufts 6 comprise fibers that are integral with and extend from the fibers of the either precursor web 20 or 21.

Therefore, from the above description, it is understood that in one embodiment web 1 can be described as being a laminate web formed by selective mechanical deformation of at least a first and second precursor webs, at least the first precursor web being a nonwoven web, the laminate web having a first side, the first side comprising the second precursor web and a plurality of discrete tufts, each of the discrete tufts comprising a plurality of tufted fibers being integral extensions of at least the first precursor web and extending through the second precursor web; and a second side, the second side comprising the first precursor web.

The extension of fibers 8 or 18 can be accompanied by a general reduction in fiber cross sectional dimension (e.g., diameter for round fibers) due to plastic deformation of the fibers and Poisson's ratio effects. Therefore, the aligned looped fibers 8 of tuft 6 can have an average fiber diameter less than the average fiber diameter of the fibers of first or second precursor webs 20 or 21. It has been found that the reduction in fiber cross-sectional dimension is greatest intermediate the base 17 and the distal portion 3 of tuft 6. This is believed to be due to the preferred method of making, as disclosed more fully below. Briefly, it is believed that portions of fibers at the base 5 and distal portion 3 of tufts 6 are adjacent the tip of teeth 110 of roll 104, described more fully below, and are frictionally locked and immobile during processing. Thus, the intermediate portions of tufts 6 are more free to stretch, or elongate, and accordingly, can experience a corresponding fiber cross sectional dimension reduction.

Figure 5:
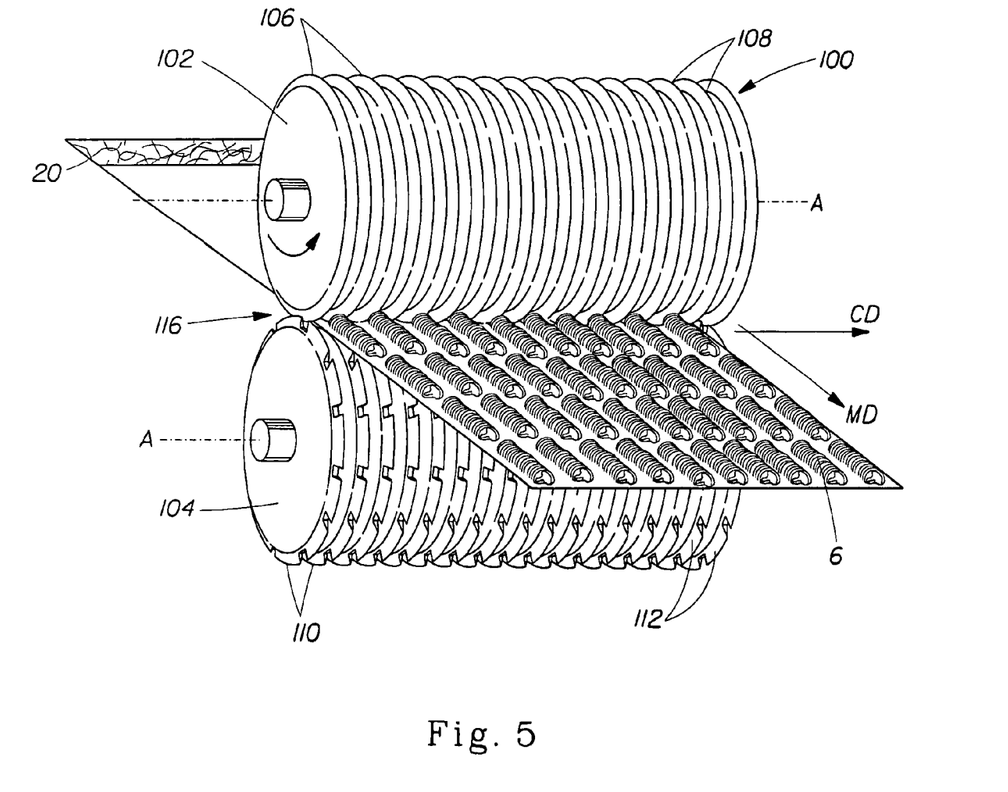
FIG. 5 is a perspective view of an apparatus for forming the web for use in the present invention.

Referring to FIG. 5 there is shown in an apparatus and method for making web 1. The apparatus 100 comprises a pair of intermeshing rolls 102 and 104, each rotating about an axis A, the axes A being parallel in the same plane. Roll 102 comprises a plurality of ridges 106 and corresponding grooves 108 which extend unbroken about the entire circumference of roll 102. Roll 104 is similar to roll 102, but rather than having ridges that extend unbroken about the entire circumference, roll 104 comprises a plurality of rows of circumferentially-extending ridges that have been modified to be rows of circumferentially-spaced teeth 110 that extend in spaced relationship about at least a portion of roll 104. The individual rows of teeth 110 of roll 104 are separated by corresponding grooves 112. In operation, rolls 102 and 104 intermesh such that the ridges 106 of roll 102 extend into the grooves 112 of roll 104 and the teeth 110 of roll 104 extend into the grooves 108 of roll 102. The intermeshing is shown in greater detail in the cross sectional representation of FIG. 6, discussed below. Both or either of rolls 102 and 104 can be heated by means known in the art such as by using hot oil filled rollers or electrically-heated rollers.

In FIG. 5, the apparatus 100 is shown in a preferred configuration having one patterned roll, e.g., roll 104, and one non-patterned grooved roll 102. However, in certain embodiments it may be preferable to use two patterned rolls 104 having either the same or differing patterns, in the same or different corresponding regions of the respective rolls. Such an apparatus can produce webs with tufts 6 protruding from both sides of the web 1.

The method of making a web 1 in a commercially viable continuous process is depicted in FIG. 5. Web 1 is made by mechanically deforming precursor webs, such as first and second precursor webs, 20 and 21 that can each be described as generally planar and two dimensional prior to processing by the apparatus shown in FIG. 5. By "planar" and "two dimensional" is meant simply that the webs start the process in a generally flat condition relative to the finished web 1 that has distinct, out-of-plane, Z-direction three-dimensionality due to the formation of tufts 6. "Planar" and "two-dimensional" are not meant to imply any particular flatness, smoothness or dimensionality.

The process and apparatus of the present invention is similar in many respects to a process described in U.S. Pat. No. 5,518,801 entitled "Web Materials Exhibiting Elastic-Like Behavior" and referred to in subsequent patent literature as "SELF" webs, which stands for "Structural Elastic-like Film". However, there are significant differences between the apparatus and process of the present invention and the apparatus and process disclosed in the '801 patent, and the differences are apparent in the respective webs produced thereby. As described below, the teeth 110 of roll 104 have a specific geometry associated with the leading and trailing edges that permit the teeth to essentially "punch" through the precursor webs 20, 21 as opposed to, in essence, deforming the web. In a two layer laminate web 1 the teeth 110 urge fibers from precursor webs 20 and 21 out-of-plane by the teeth 110 pushing the fibers 8 through to form tufts 6. Therefore, a web 1 can have tufts 6 comprising loose fiber ends 18 and/or "tunnellike" tufts 6 of looped, aligned fibers 8 extending away from the surface 13 of side 3, unlike the "tent-like" rib-like elements of SELF webs which each have continuous side walls associated therewith, i.e., a continuous "transition zone," and which do not exhibit interpenetration of one layer through another layer.

Precursor webs 20 and 21 are provided either directly from their respective web making processes or indirectly from supply rolls (neither shown) and moved in the machine direction to the nip 116 of counter-rotating intermeshing rolls 102 and 104. The precursor webs are preferably held in a sufficient web tension so as to enter the nip 16 in a generally flattened condition by means well known in the art of web handling. As each precursor web 20, 21 goes through the nip 116 the teeth 110 of roll 104 which are intermeshed with grooves 108 of roll 102 simultaneously urge portions of precursor webs 20 and 21 out of the plane to form tufts 6. In one embodiment, teeth 110 in effect "push" or "punch" fibers of first precursor web 20 through second precursor web 21. In another embodiment teeth 110 in effect "push" or "punch" fibers of both first and second precursor webs 20 and 21 out of plane to form tufts 6.

As the tip of teeth 110 push through first and second precursor webs 20, 21 the portions of the fibers of first precursor web 20 (and, in some embodiments, second precursor web 21) that are oriented predominantly in the CD across teeth 110 are urged by the teeth 110 out of the plane of first precursor web 20. Fibers can be urged out of plane due to fiber mobility, or they can be urged out of plane by being stretched and/or plastically deformed in the Z-direction. Portions of the precursor webs urged out of plane by teeth 110 results in formation of tufts 6 on first side 3 of web 1. Fibers of precursor webs 20 and 21 that are predominantly oriented generally parallel to the longitudinal axis L, i.e., in the MD as shown in FIG. 1, are simply spread apart by teeth 110 and remain substantially in their original, randomly-oriented condition. This is why the looped fibers 8 can exhibit the unique fiber orientation in embodiments such as the one shown in FIGS. 1-4, which is a high percentage of fibers of each tuft 6 having a significant or major vector component parallel to the transverse axis T of tuft 6.

It can be appreciated by the forgoing description that when web 1 is made by the apparatus and method of the present invention that the precursor webs 20, 21 can possess differing material properties with respect to the ability of the precursor webs to elongate before failure, e.g., failure due to tensile stresses. In one embodiment, a nonwoven first precursor web 20 can have greater fiber mobility and/or greater fiber elongation characteristics relative to second precursor web 21, such that the fibers thereof can move or stretch sufficiently to form tufts 6 while the second precursor web 21 ruptures, i.e., does not stretch to the extent necessary to form tufts. In another embodiment, second precursor web 21 can have greater fiber mobility and/or greater fiber elongation characteristics relative to first precursor web 20, such that both first and second precursor webs 20 and 21 form tufts 6. In another embodiment, second precursor web 21 can have greater fiber mobility and/or greater fiber elongation characteristics relative to first precursor web 20, such that the fibers of second precursor web 21 can move or stretch sufficiently to form tufts 6 while the first precursor web 20 ruptures, i.e., does not stretch to the extent necessary to form tufts.

The degree to which the fibers of nonwoven precursor webs are able to extend out of plane without plastic deformation can depend upon the degree of inter-fiber bonding of the precursor web. For example, if the fibers of a nonwoven precursor web are only very loosely entangled to each other, they will be more able to slip by each other (i.e., to move relative to adjacent fibers by reptation) and therefore be more easily extended out of plane to form tufts. On the other hand, fibers of a nonwoven precursor web that are more strongly bonded, for example by high levels of thermal point bonding, hydroentanglement, or the like, will more likely require greater degrees of plastic deformation in extended out-of-plane tufts. Therefore, in one embodiment, one precursor web 20 or 21 can be a nonwoven web having relatively low inter-fiber bonding, and the other precursor web 20 or 21 can be a nonwoven web having relatively high inter-fiber bonding, such that the fibers of one precursor web can extend out of plane, while the fibers of the other precursor web cannot.

In one embodiment, for a given maximum strain (e.g., the strain imposed by teeth 110 of apparatus 100), it is beneficial that second precursor web 21 actually fail under the tensile loading produced by the imposed strain. That is, for the tufts 6 comprising only, or primarily, fibers from first precursor web 20 to be disposed on the first side 3 of web 1, second precursor web 21 must have sufficiently low fiber mobility (if any) and/or relatively low elongation-to-break such that it locally (i.e., in the area of strain) fails in tension, thereby producing openings 4 through which tufts 6 can extend.

In another embodiment it is beneficial that second precursor web 21 deform or stretch in the region of induced strain, and does not fail, such that tuft 6 includes portions of second precursor web 21.

In one embodiment second precursor web 21 has an elongation to break in the range of 1%-5%. While the actual required elongation to break depends on the strain to be induced to form web. 1, it is recognized that for most embodiments, second precursor web 21 can exhibit a web elongation-to-break of 6%, 7%, 8%, 9%, 10%, or more. It is also recognized that actual elongation-to-break can depend on the strain rate, which, for the apparatus shown in FIG. 5 is a function of line speed. Elongation to break of webs used in the present invention can be measured by means known in the art, such as by standard tensile testing methods using standard tensile testing apparatuses, such as those manufactured by Instron, MTS, Thwing-Albert, and the like.

Relative to first precursor web 20, second precursor web 21 can have lower fiber mobility (if any) and/or lower elongation-to-break (i.e., elongation-to-break of individual fibers, or, if a film, elongation-to-break of the film) such that, rather than extending out-of-plane to the extent of the tufts 6, second precursor web 21 fails in tension under the strain produced by the formation of tufts 6, e.g., by the teeth 110 of apparatus 100. In one embodiment, second precursor web 21 exhibits sufficiently low elongation-to-break relative to first precursor web 20 such that flaps 7 of opening 4 only extend slightly out-of-plane, if at all, relative to tufts 6. In general, for embodiments in which tufts 6 comprise primarily fibers from first precursor web 20, it is believed that second precursor web 21 should have an elongation to break of at least 10% less than the first precursor web 20, preferably at least 30% less, more preferably at least 50% less, and even more preferably at least about 100% less than that of first precursor web 20. Relative elongation to break values of webs used in the present invention can be measured by means known in the art, such as by standard tensile testing methods using standard tensile testing apparatuses, such as those manufactured by Instron, MTS, Thwing-Albert, and the like.

In one embodiment second precursor web 21 can comprise substantially all MD-oriented fibers, e.g., tow fibers, such that there are substantially no fibers oriented in the CD. For such an embodiment of web 1 the fibers of second precursor web 21 can simply separate at the opening 4 through which tufts 6 extend. In this embodiment, therefore, second precursor web 21 need not have any minimum elongation to break, since failure or rupture of the material is not the mode of forming opening 4.

The number, spacing, and size of tufts 6 can be varied by changing the number, spacing, and size of teeth 110 and making corresponding dimensional changes as necessary to roll 104 and/or roll 102. This variation, together with the variation possible in precursor webs 20, 21 permits many varied webs 1 having varied fluid handling properties for use in a disposable absorbent article. As described more fully below, a web 1 comprising a nonwoven/film first precursor web/second precursor web combination can also be used as a component in disposable absorbent articles. However, even better results are obtained in a nonwoven/nonwoven precursor web/second precursor web combination wherein fibers from both webs contribute to tufts 6.

Figure 6:
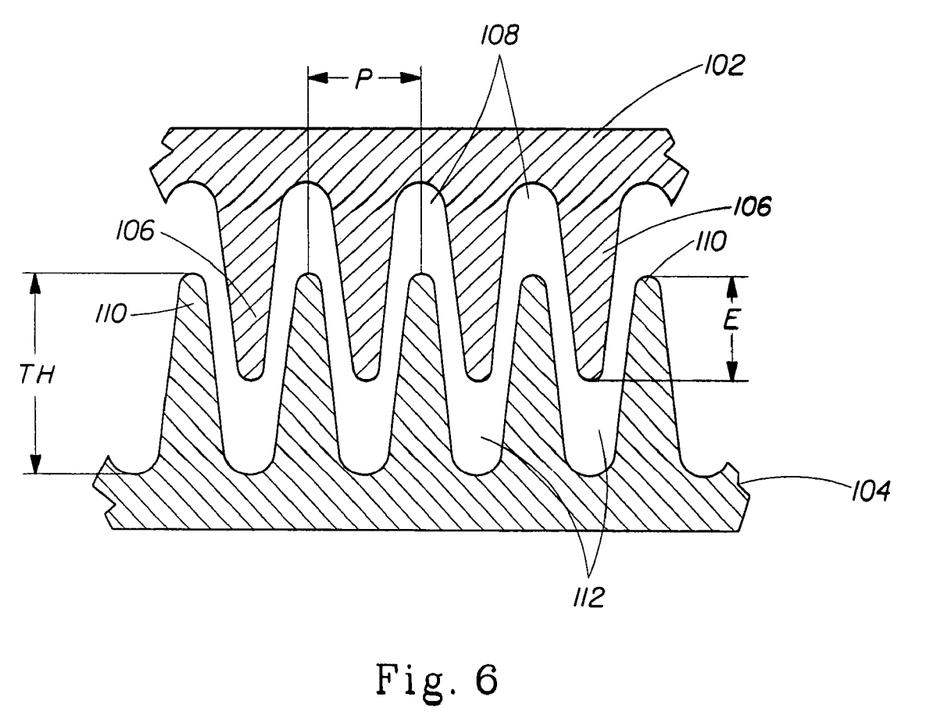
FIG. 6 is a cross-sectional depiction of a portion of the apparatus shown in FIG. 5.

FIG. 6 shows in cross section a portion of the intermeshing rolls 102 and 104 and ridges 106 and teeth 110. As shown teeth 110 have a tooth height TH (note that TH can also be applied to ridge height; in a preferred embodiment tooth height and ridge height are equal), and a tooth-to-tooth spacing (or ridge-to-ridge spacing) referred to as the pitch P. As shown, depth of engagement E is a measure of the level of intermeshing of rolls 102 and 104 and is measured from tip of ridge 106 to tip of tooth 110. The depth of engagement E, tooth height TH, and pitch P can be varied as desired depending on the properties of precursor webs 20, 21 and the desired characteristics of web 1. For example, in general, the greater the level of engagement E, the greater the necessary elongation or fiber-to-fiber mobility characteristics the fibers of portions of the precursor webs intended to form tufts must possess. Also, the greater the density of tufts 6 desired (tufts 6 per unit area of web 1), the smaller the pitch should be, and the smaller the tooth length TL and tooth distance TD should be, as described below.

Figure 7:
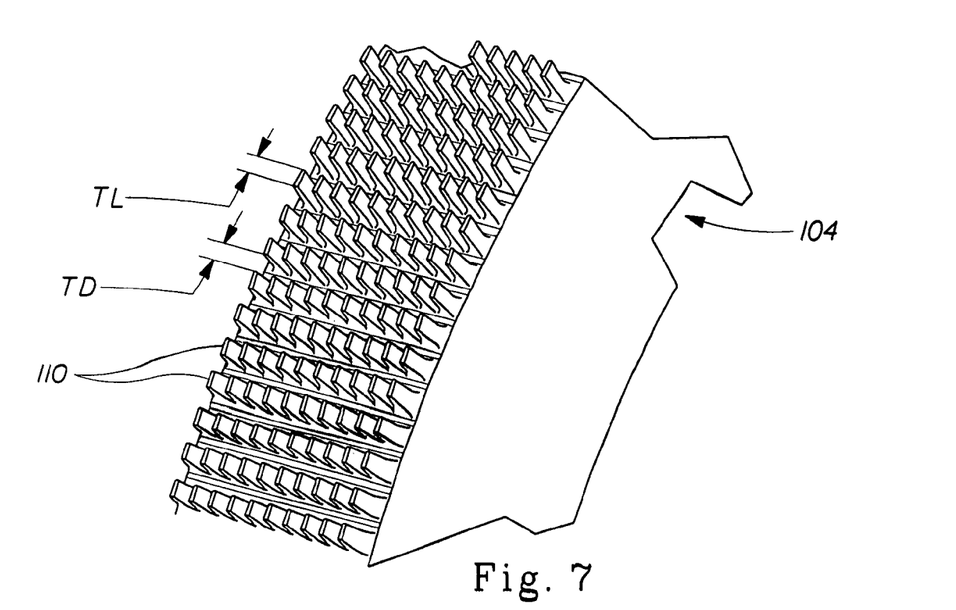
FIG. 7 is a perspective view of a portion of the apparatus for forming one embodiment of a web suitable for use in an article of the present invention.

FIG. 7 shows one embodiment of a roll 104 having a plurality of teeth 110 useful for making a web 1 from a nonwoven first precursor web 20 having a basis weight of between about 60 gsm and 100 gsm, preferably about 80 gsm and a polyolefinic film (e.g., polyethylene or polypropylene) second precursor web 21 having a density of about 0.91-0.94 and a basis weight of about 20 gsm.

Figure 8:
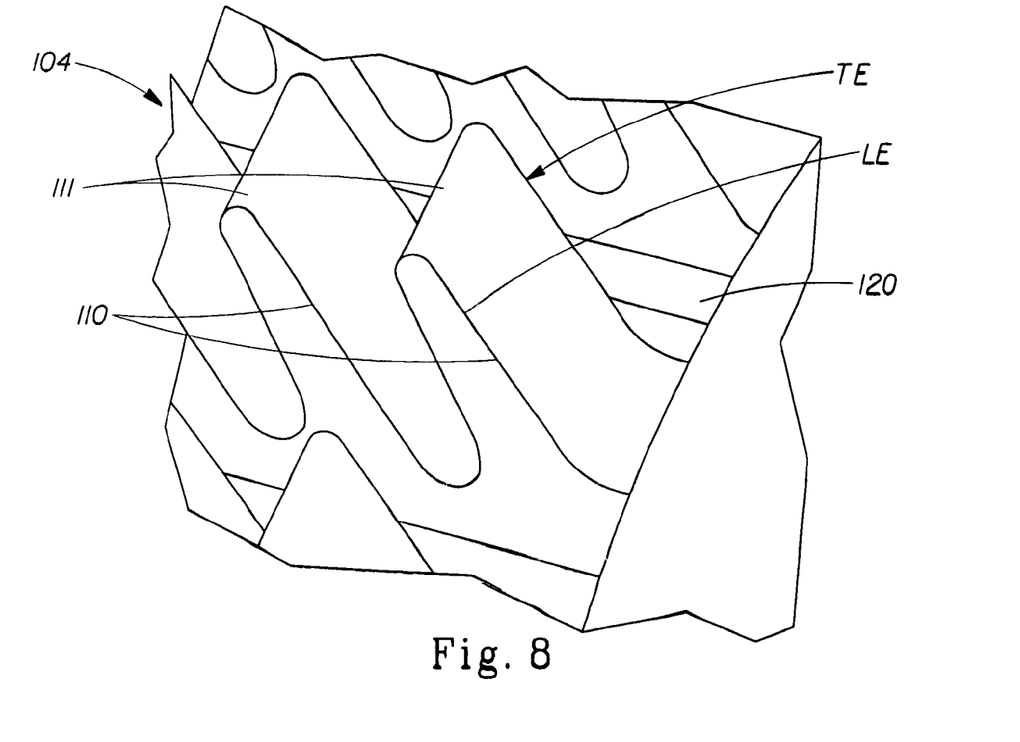
FIG. 8 is an enlarged perspective view of a portion of the apparatus for forming a web suitable for use in an article of the present invention.

An enlarged view of teeth 110 is shown in FIG. 8. In this embodiment of roll 104 teeth 110 have a uniform circumferential length dimension TL measured generally from the leading edge LE to the trailing edge TE at the tooth tip 111 of about 1.25 mm and are uniformly spaced from one another circumferentially by a distance TD of about 1.5 mm. For making a terry-cloth web 1 from web 1 having a total basis weight in the range of about 60 to about 100 gsm, teeth 110 of roll 104 can have a length TL ranging from about 0.5 mm to about 3 mm and a spacing TD from about 0.5 mm to about 3 mm, a tooth height TH ranging from about 0.5 mm to about 5 mm, and a pitch P between about 1 mm (0.040 inches) and about 5 mm (0.200 inches). Depth of engagement E can be from about 0.5 mm to about 5 mm (up to a maximum equal to tooth height TH). Of course, E, P, TH, TD and TL can be varied independently of each other to achieve a desired size, spacing, and area density of tufts 6 (number of tufts 6 per unit area of web 1).

As shown in FIG. 8, each tooth 110 has a tip 111, a leading edge LE and a trailing edge TE. The tooth tip 111 is elongated and has a generally longitudinal orientation, corresponding to the longitudinal axes L of tufts 6 and discontinuities 16. It is believed that to get the tufted, looped tufts 6 of the web 1 that can be described as being terry cloth-like, the LE and TE should be very nearly orthogonal to the local peripheral surface 120 of roll 104. As well, the transition from the tip 111 and LE or TE should be a sharp angle, such as a right angle, having a sufficiently small radius of curvature such that teeth 110 push through second precursor web 21 at the LE and TE. Without being bound by theory, it is believed that having relatively sharply angled tip transitions between the tip of tooth 110 and the LE and TE permits the teeth 110 to punch through precursor webs 20, 21 "cleanly", that is, locally and distinctly, so that the first side 3 of the resulting web 1 can be described as "tufted" rather than "deformed." When so processed, the web 1 is not imparted with any particular elasticity, beyond what the precursor webs 20 and 21 may have possessed originally.

Figure 9:
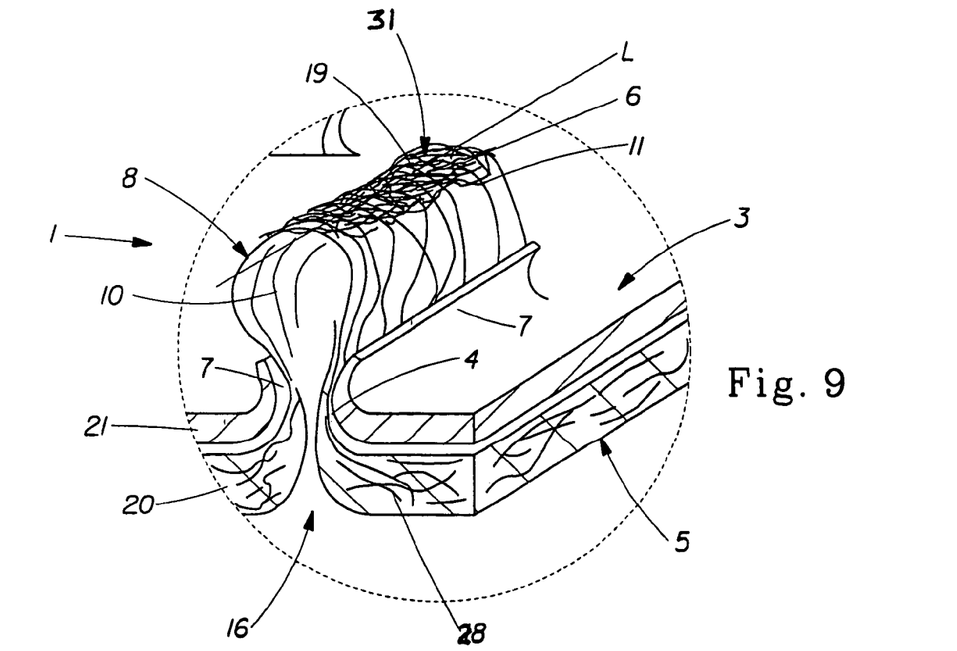
FIG. 9 is an enlarged view of a portion of another embodiment of a web suitable for use in an article of the present invention.

At higher line speeds, i.e., relatively higher rates of processing of the web through the nip of rotating rolls 102 and 104, like materials can exhibit very different structures for tufts 6. The tuft 6 shown in FIG. 9 is similar in structure to the tuft shown in FIG. 2 but exhibits a very different structure, a structure that appears to be typical of spunbond nonwoven first precursor webs 20 processed to form tufts 6 at relatively high speeds, i.e., at high strain rates. Typical of this structure is broken fibers between the proximal portion, i.e., base 7, of tufts 6 and the distal portion, i.e., the top 31, of tuft 6, and what appears to be a "mat" 19 of fibers at the top of the tuft 6. Mat 19 comprises and is supported at the top of tufts 6 by unbroken, looped fibers 8, and also comprises portions of broken fibers 11 that are no longer integral with first precursor web 20. That is, mat 19 comprises fiber portions which were formerly integral with precursor web 20 but which are completely detached from precursor web 20 after processing at sufficiently high line speeds, e.g., 30 meters per minute line speed in the process described with reference to FIG. 5.

Therefore, from the above description, it is understood that in one embodiment web 1 can be described as being a laminate web formed by selective mechanical deformation of at least a first and second precursor webs, at least the first precursor web being a nonwoven web, the laminate web having a first garment-facing, side, the first garment-facing side comprising the second precursor web and a plurality of discrete tufts, each of the discrete tufts comprising fibers integral with but extending from the first precursor web and fibers neither integral with nor extending from the first precursor web.

Although it is believed that the distinct fiber orientation observed at the distal portion of tufts 6, e.g., mat 19, is due primarily to processing rates, it is also believed to be affected by other parameters, such as fiber type and basis weight of the precursor webs 20 and 21 as well as processing temperatures that can affect the degree of fiber-to-fiber bonding. Matting of fibers is believed to occur on the portion of tuft 6 associated during manufacturing with the tip of tooth 110 of roll 104. It is believed that frictional engagement of the fibers at the tip of the teeth "lock" the fibers in place, thereby limiting fiber elongation and/or fiber mobility, two mechanisms believed to permit formation of tufts 6. Therefore, once locked, so to speak, in position, fibers adjacent tooth 110 tip can be broken, and, due to the random entanglement of the precursor web as well as possible cold welding of fibers due to pressure and friction, the broken fibers 11 become and remain lodged in mat 19 at the distal end 3 of tufts 6.

Precursor webs having relatively higher basis weights generally have relatively more fiber 11 portions in mat 19. In one sense, it appears as if most of the fiber content of the precursor webs in the immediate vicinity of a tooth tip 110 during manufacture can be simply displaced in the Z-direction to the distal portion 3 of tufts 6, resulting in mat 19. First precursor webs 20 comprising relatively low elongation fibers, or fibers with relatively low fiber-to-fiber mobility (e.g., relatively limited capability for fiber reptation) appear to result in relatively few fibers becoming and remaining lodged in mat 19 at the distal end 3 of tufts 6. Fiber-to-fiber mobility can be increased by reducing or eliminating the fiber-to-fiber bonds. Thermal bonds can be completely eliminated (i.e., avoided by not bonding), or significantly reduced in certain nonwoven webs to increase fiber-to-fiber mobility. Similarly, hydroentangled webs can be less entangled to increase fiber-to-fiber mobility. For any precursor web 20, lubricating it prior to processing as disclosed herein can also increase fiber-to-fiber mobility. For example, a mineral oil lubricant can be applied to first precursor web 20 prior to it entering the nip 116 of rolls 102 and 104. Additionally, a plasticizing agent, such as petrolatum, can be added to some synthetic fiber webs, such as polyethylene or a polyethylene and polypropylene web, to increase extensibility.

While not wishing to be bound by theory, it is believed that if the fibers of the first precursor web have a highly curvilinear shape, e.g., curled or crimped fibers, the resultant tufts 6 will have more looped fibers 8 and less broken fibers 18 as compared to more linear fiber conformations. It is believed that such fiber conformations have a lesser chance of bridging between two adjacent teeth, and, as a result they are less prone to be stretched beyond their breaking point, and thus have a greater chance of forming complete loop structures. Furthermore, such curvilinear-shaped fibers can be made by using eccentric bicomponent fibers, or side-by-side bicomponent fibers, such as bicomponent fibers consisting of polyethylene and nylon.

Figure 10:
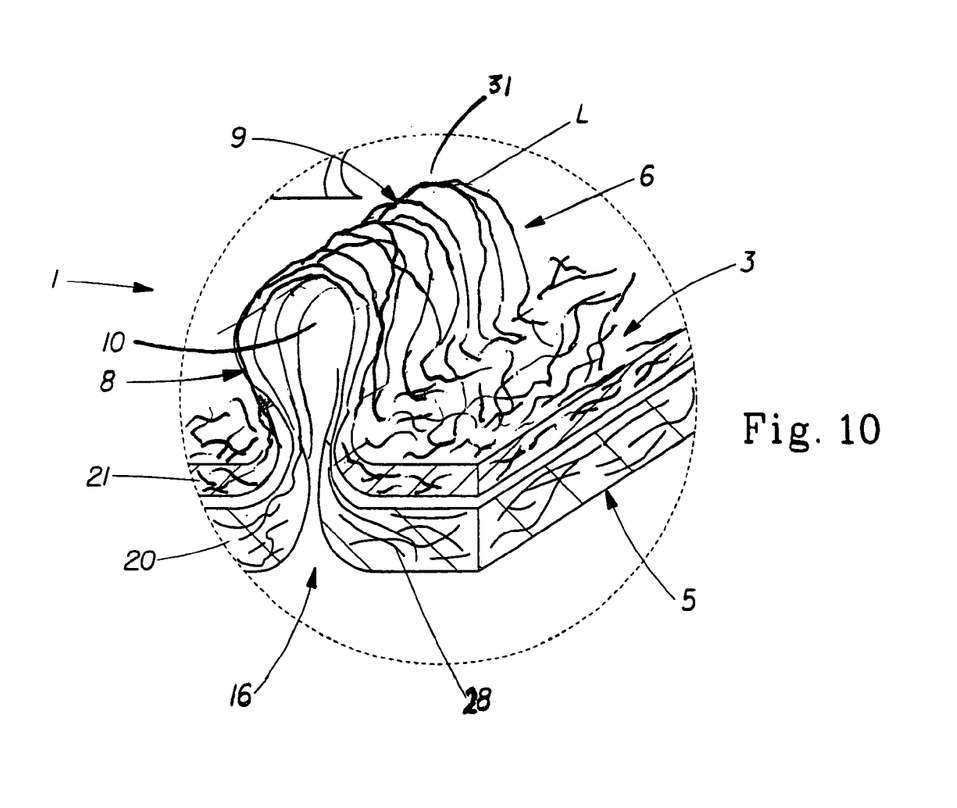
FIG. 10 is an enlarged view of a portion of another embodiment of a web suitable for use in an article of the present invention.

In another embodiment of web 1, after forming tufts 6 by the process described above, the distal portions 3 of tufts 6 are heated to thermally join portions of discrete fibers such that adjacent fiber portions are joined to one another to form tufts 6 having distally-disposed melt-bonded portions 9, as depicted in FIG. 10.

It has been found that certain nonwoven webs, such as carded webs comprising staple-length fibers, when used as a precursor web produce very few looped fibers 8 in tufts 6, so that the tufts 6 produced in these webs may not be described as comprising a plurality of looped, aligned fibers 8 as described above with respect to FIGS. 1-4. Instead, carded nonwoven webs can produce tufts 6 having few, if any, looped, aligned fibers 8, and many, if not all, non-aligned fibers and/or broken fibers 18. It is believed that the non-alignment of fibers in tufts 6 made from carded webs is due in part to the nature of the fiber content of carded webs. Staple fibers are not "endless," but instead have a predetermined length on the order of about 15 mm to about 100 mm, and, more typically from about 40 mm to about 80 mm. Therefore, when a carded web is processed by the apparatus described with respect to FIG. 5, it is believed that there is a much greater likelihood that a loose fiber end will be in the vicinity of a tuft 6 and thus produce a non-looped fiber end in tuft 6. Furthermore, often staple fibers do not have the same elongation characteristics of spunbond or meltblown fibers, for example. However, even if tufts 6 have no looped fibers, the fibrous tufts can nevertheless provide a softness benefit and produce a web useful for use in a disposable absorbent article.

In preferred embodiments precursor webs are nonwoven webs in which there are minimal fiber-to-fiber bonds. For example, the precursor web can be a nonwoven web having a pattern of discrete thermal point bonds, as is commonly known in the art for nonwoven webs. In general, however, it is believed to be desirable to minimize the number of bond points and maximize the spacing so as to allow for maximum fiber mobility and dislocation at during formation of tufts 6. In general, utilizing fibers having relatively high diameters, and/or relatively high extension to break, and/or relatively high fiber mobility, results in better and more distinctly formed tufts 6.

Although web 1 is disclosed in preferred embodiments as a two layer web made from two precursor webs, it is not necessary that it be limited to two layers. For example, a three-layer or more laminate can be made from three or more precursor webs, as long as one of the precursor webs can extend out-of-plane to form tufts on a garment-facing side thereof. In general, it is not necessary that adhesive or other bonding means be utilized to make laminate web 1. The constituent layers of web 1 (e.g., precursor webs 20 and 21 and any other layers) can be held in a face-to-face laminated relationship by virtue of the "locking" effect of the tufts 6 that extend through openings 4 in second precursor web 21. In some embodiments it may be desirable to use adhesives or thermal bonding or other bonding means, depending on the end use application of web 1. For example, a web 1 comprising bicomponent fiber nonwoven webs can be through-air bonded after formation of tufts 6 to provide for layer-to-layer adhesion for greater peel strength. Additionally, it may be desirable to apply adhesive to a portion of one of the precursor webs. For example, in some embodiments adhesive or thermal bonding between layers can be selectively applied to certain regions of web 1. In the case of adhesive application, for example, adhesive can be applied in a continuous manner, such as by slot coating, or in a discontinuous manner, such as by spraying, extruding, and the like. Discontinuous application of adhesive can be in the form of stripes, bands, droplets, and the like.

In a multilayer web 1 each precursor web can have different material properties, thereby providing web 1 with beneficial properties with respect to use as a topsheet in a disposable absorbent article, as described more fully below. For superior fluid handling, for example, first precursor web 20 can be comprised of relatively hydrophilic fibers. Second precursor web 21 can be polymer film, e.g., a polyethylene film, and can be hydrophobic or rendered hydrophobic. The tufts 6 of such a web could form an upper layer, i.e., a body-contacting layer when used as a topsheet on a disposable absorbent article. Fluid deposited upon the upper, relatively hydrophilic tufts is quickly transported away from the relatively hydrophobic film to the portion of the first precursor web underlying the second film precursor web layer. One reason for the observed rapid fluid transport is the capillary structures formed by the generally aligned fibers 8, 18 of tufts 6. The fibers 8, 18 form directionally-aligned capillaries between adjacent fibers, and the capillary action is enhanced by the general convergence of fibers near proximal portion 7 of tufts 6.

In one embodiment, web 1 comprises a nonwoven first precursor web 20 comprising a spunbond nonwoven having a basis weight of about 80 gsm, and comprising polyethylene/polypropylene (sheath/core) bicomponent fibers having an average diameter of about 33 microns, and a second precursor web comprising a polyethylene film having a basis weight of 20 gsm. In this embodiment, web 1 has about 24 tufts 6 per square centimeter, the tufts 6 having a plurality of looped, aligned fibers 8, each of which has an average fiber diameter of about 18 microns. A web of this type can be beneficially used as a topsheet for disposable absorbent articles, as shown below with reference to FIG. 11. For example, such a web 1 is fluid impermeable except in the regions of the tufts 6 which permit wicking of fluid from the second body-facing side 5 of web 1 to the first garment-facing side 3.

In one embodiment, as depicted schematically in FIG. 10, two nonwoven precursor webs can be used, each precursor web having sufficient fiber mobility or elongation such that tufts 6 comprise fibers from each precursor web.

Figure 11:
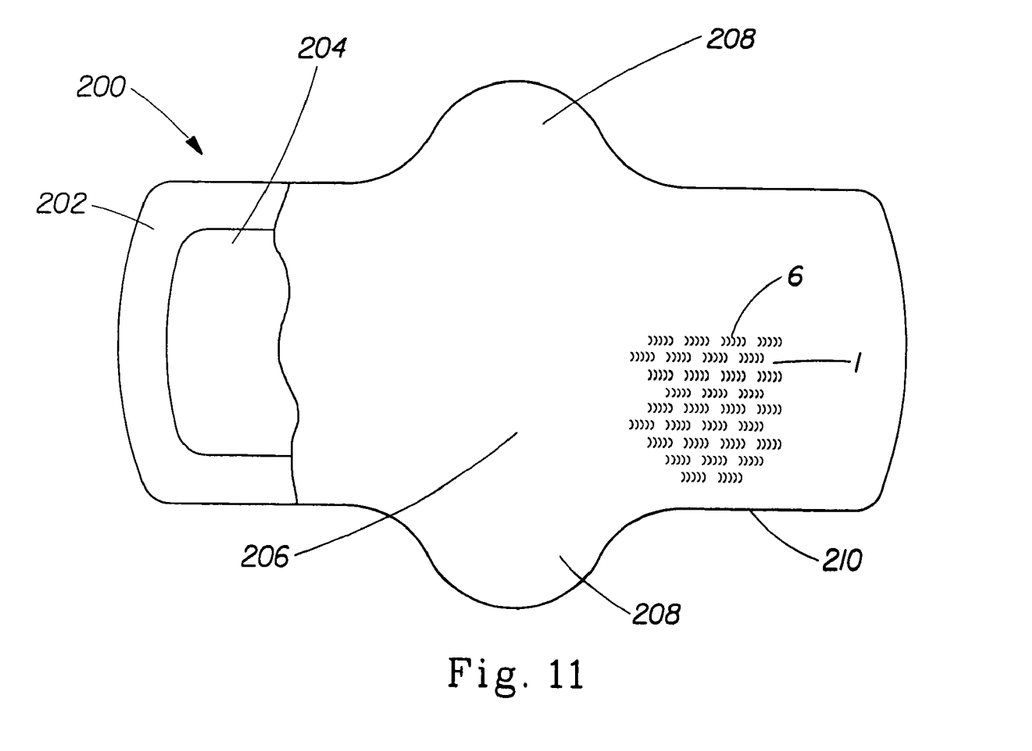
FIG. 11 is a partial cut away plan view of a sanitary napkin of the present invention.

FIG. 11 shows in partial cut away plan view a sanitary napkin having as one of its components a web 1 of the present invention. In general, sanitary napkin 200 comprises a backsheet 202, a topsheet 206 and an absorbent core 204 disposed between the topsheet 206 and backsheet 202 which can be joined about a the periphery 210. Sanitary napkin 1 can have side extensions, commonly referred to as "wings" 208 designed to wrap the sides of the crotch region of the panties of the user of sanitary napkin 1. Sanitary napkins, including topsheets for use as the body facing surface thereof, are well known in the art and need no detailed description of various alternative and optional designs. However, it is noted that web 1 can be used as, or as a component of, one or more of a backsheet, core material, topsheet, secondary topsheet, or wing material.

Web 1 is especially useful as a topsheet 206 of sanitary napkin 200. As described above, a topsheet 206 comprising a web of the present invention made by using a relatively hydrophilic nonwoven first precursor web 20 and a relatively hydrophobic second precursor web 21 provides for a topsheet 206, that when viewed in plan view as in FIG. 11 presents a substantially hydrophilic body-facing surface. The topsheet 206 can comprise two layers, i.e., one layer corresponding to each precursor web, and the second precursor web could be considered to be a secondary topsheet. But since the two webs are joined into a laminate composite, they are referred to herein as a topsheet 206. The basis weights of the precursor webs can be varied due to cost and benefit considerations. In general, a web 1 having a total basis weight of between about 20 gsm and 100 gsm is desirable for use as a topsheet 206 in a disposable absorbent article, such as a sanitary napkin. Second precursor web 21 can be a nonwoven web or a polymer film web. When made as a hydrophilic/hydrophobic (one web with respect to the other) nonwoven/film laminate, web 1 has been found to combine the softness and fluid capillarity of fiber tufts with the rewet prevention of a fluid impermeable polymer film. Likewise, when made as a hydrophilic/hydrophobic (one web with respect to the other) nonwoven/nonwoven laminate, web 1 has also been found to combine consumer-acceptable softness with excellent gush fluid acquisition and rewet properties.

Web 1 is also useful as a fluid storage element, such as core 204 of sanitary napkin 200 shown in FIG. 11. In particular, a core material comprising a relatively high caliper airfelt or nonwoven material for the second precursor web, such that tufts 6 do not actually extend through second precursor web. In one embodiment, absorbent core 204 is effective when first side 3 of web 1 is a garment-facing side, such that discontinuities 16 are effective in channeling fluid into the interior of the core 204.

Figure 12:
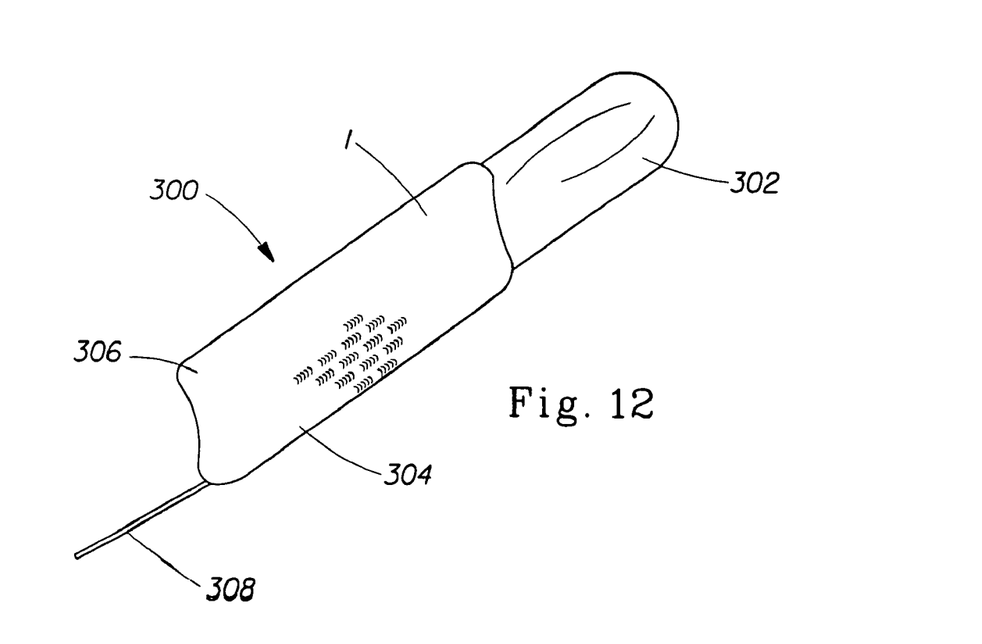
FIG. 12 is a partial cut away perspective view of a tampon of the present invention.

FIG. 12 shows in partial cut away perspective view a catamenial tampon 300 having as one of its components a web 1 of the present invention. In general, tampon 300 comprises a compressed absorbent core 302 and a fluid permeable cover wrap 304 that covers absorbent core 302. Cover wrap 304 may extend beyond one end of absorbent core 302 to form a skirt portion 306. A removal means, such as string 308 can be provided to facilitate removal of the tampon after use. Tampons, including cover wraps for use as the body contacting surface thereof, are well known in the art and need no detailed description of various alternative and optional designs. However, it is noted that web 1 can be used as, or as a component of, one or more of a cover wrap, absorbent core material, or removal means material. When used in a tampon it is noted that there is not technically a "garment-facing" side of web 1, and, therefore, in a tampon first side 3 is an "interiorly-oriented" side and second side 3 is an "exteriorly-oriented" side of web 1.

As can be understood from the above description of webs 1 and apparatus 100 of the present invention, many various structures of webs 1 can be made without departing from the scope of the present invention as claimed in the appended claims. For example, webs 1 can be coated or treated with lotions, medications, cleaning fluids, anti-bacterial solutions, emulsions, fragrances, surfactants. In particular, relatively hydrophobic lotion having a hydrophilic/lipophilic balance (HLB) of less than or equal to 7. The lotion can be petrolatum-based and can comprise skin treatment agents and other ingredients as disclosed commonly-assigned U.S. patent application Ser. No. 10/444,241.

Apparatus 100 can be configured to only form tufts 6 on a portion of the web 1, or to form varying sizes or area densities of tufts 6.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composite web adapted for use as a component in a disposable absorbent article, said composite web comprising a first fibrous layer and a second layer, said first and second layers each comprising a body-facing side and a garment-facing side and being disposed in a face to face relationship to form a laminate, said first fibrous layer comprising a fibrous web of randomly oriented fibers with respect to a MD-CD plane, and comprising a plurality of discrete regions of fiber reorientation at least on said body-facing side, and comprising a plurality of fibers having portions reoriented in a direction substantially orthogonal to said MD-CD plane and extending toward said garment-facing side of said second layer, and wherein each said discrete region has a distinct linear orientation in said MD-CD plane and a longitudinal axis in said MD-CD plane, wherein said composite web is disposed between a topsheet and a backsheet.

2. The composite web of claim 1, wherein said second layer is a fibrous layer.

3. The composite web of claim 2, wherein the first fibrous layer or the second fibrous layer are nonwoven webs comprising fibers that differ in one or more properties selected from the group consisting of: basis weight, caliper, fiber type, fiber size, fiber surface energy, and hydrophobicity.

4. The composite web of claim 3, wherein the first fibrous layer or the second fibrous layer is chosen from the group consisting of, an airlaid nonwoven web, a spunbond nonwoven web, a meltblown nonwoven web, and a carded nonwoven web.

5. The composite web of claim 3, wherein said fibers of either said first or second layer comprise polymers selected from the group consisting of polyethylene, polypropylene, polyester, and blends thereof.

6. The composite web of claim 3, wherein said fibers of either said first or second layer comprise bicomponent fibers.

7. The composite web of claim 3, wherein said fibers of either said first or second layer comprise non-round fibers.

8. The composite web of claim 1 wherein said second layer is a polymer film layer.

9. The composite web of claim 8, wherein said polymer film layer is apertured.

10. The composite web of claim 1, wherein said plurality of discrete regions is uniformly distributed on said composite web.

11. The composite web of claim 1, wherein fibers having portions reoriented in a direction substantially orthogonal to said MD-CD plane and extending toward said garment-facing side extend through said second layer.

12. The composite web of claim 1, wherein fibers having portions reoriented in a direction substantially orthogonal to said MD-CD plane and extending toward said garment-facing side do not extend through said second layer.

13. An absorbent core for a disposable absorbent article, the absorbent core comprising a first fibrous layer and a second layer, said first and second layers each comprising a body-facing side and a garment-facing side and being disposed in a face to face relationship to form a laminate, said first fibrous layer comprising a fibrous web of randomly oriented fibers with respect to an MD-CD plane, and comprising a plurality of discrete regions of fiber reorientation at least on said body-facing side, and comprising a plurality of fibers having portions reoriented in a direction substantially orthogonal to said MD-CD plane and extending toward said garment-facing side of said second layer, and wherein each said discrete region has a distinct linear orientation in said MD-CD plane and a longitudinal axis in said MD-CD plane, wherein said absorbent core is disposed between a topsheet and a backsheet.

14. The absorbent core of claim 13, wherein said second layer is a fibrous layer.

15. The absorbent core of claim 13, wherein said first fibrous layer has an average fiber diameter and said discrete regions have an average fiber diameter, wherein said average fiber diameter of said discrete regions is less than said average fiber diameter of said first fibrous layer.

16. A topsheet for a disposable absorbent article, the topsheet comprising a first fibrous layer and a second layer, said first layer relatively hydrophobic compared to said second layer, said first and second layers each comprising a body-facing side and a garment-facing side and being disposed in a face to face relationship to form a laminate, said first fibrous layer comprising a fibrous web of randomly oriented fibers with respect to a MD-CD plane, and comprising a plurality of discrete regions of fiber reorientation at least on said body-facing side, and comprising a plurality of fibers having portions reoriented in a direction substantially orthogonal to said MD-CD plane and extending toward said garment-facing side of said second layer, and wherein each said discrete region has a distinct linear orientation and a longitudinal axis in said MD-CD plane, said first fibrous layer having an average fiber diameter and said discrete regions having an average fiber diameter, wherein said average fiber diameter of said discrete regions is less than said average fiber diameter of said first fibrous layer, wherein said second layer is a fibrous layer.

17. The topsheet of claim 16 wherein said fibers having portions reoriented in a direction substantially orthogonal to said MD-CD plane and extending toward said garment-facing side of said second layer do not extend through said second layer.

* * * * *